United States Patent
Hancke Orozco et al.

(10) Patent No.: US 9,060,994 B2
(45) Date of Patent: Jun. 23, 2015

(54) COMBINATION THERAPY WITH INTERFERON AND ANDROGRAPHOLIDES FOR MULTIPLE SCLEROSIS

(71) Applicants: Juan L Hancke Orozco, Valdivia (CL); Rafael Burgos, Valdivia (CL)

(72) Inventors: Juan L Hancke Orozco, Valdivia (CL); Rafael Burgos, Valdivia (CL)

(73) Assignee: Inno Biosciences, S.p.A., Santiago (CL)

( * ) Notice: Subject to any disclaimer, the term of this patent is extended or adjusted under 35 U.S.C. 154(b) by 0 days.

(21) Appl. No.: 13/984,124

(22) PCT Filed: Dec. 19, 2012

(86) PCT No.: PCT/US2012/070568
§ 371 (c)(1),
(2) Date: Aug. 7, 2013

(87) PCT Pub. No.: WO2013/096423
PCT Pub. Date: Jun. 27, 2013

(65) Prior Publication Data
US 2014/0301981 A1    Oct. 9, 2014

Related U.S. Application Data

(60) Provisional application No. 61/578,650, filed on Dec. 21, 2011.

(51) Int. Cl.
*A61K 31/341* (2006.01)
*A61K 38/21* (2006.01)
*A61P 37/00* (2006.01)

(52) U.S. Cl.
CPC .............. *A61K 31/341* (2013.01); *A61K 38/21* (2013.01); *A61K 38/215* (2013.01)

(58) Field of Classification Search
CPC .... A61K 31/341; A61K 38/21; A61K 38/215
USPC ............................ 514/473; 549/475; 424/85.6
See application file for complete search history.

(56) References Cited

U.S. PATENT DOCUMENTS

| 2002/0032229 A1 | 3/2002 | Nanduri et al. |
| 2005/0181033 A1 | 8/2005 | Dekker, III et al. |
| 2005/0220764 A1 | 10/2005 | Abdul-Ahad et al. |
| 2006/0063831 A1 | 3/2006 | Hancke Orozco et al. |
| 2008/0108641 A1 | 5/2008 | Ajami |
| 2010/0172869 A1 | 7/2010 | Masuoka |

FOREIGN PATENT DOCUMENTS

WO    WO2011005473 A2    1/2011

OTHER PUBLICATIONS

WHO International Statistical Classification of Diseases and Related Health Problems 10th Revision, http://apps.who.int/classifications/icd10/browse/2015/en#/G35-G37 (accessed Jan. 20, 2015).*
Love, S. J. Clin. Pathol. 2006, 59, 1151-1159.*
Paty et al. Neurology 1993, 43, 662-667.*
Panitch et al. Neurology 1987, 37, 1097-1102.*
Cornuz et al. CMAJ 2006, 174 (6), 765-767.*
Schwid et al. Journal of Rehabilitation Research and Development 2002, 39 (2), 211-224.*

* cited by examiner

*Primary Examiner* — Sreeni Padmanabhan
*Assistant Examiner* — Irina Neagu
(74) *Attorney, Agent, or Firm* — Pharmaceutical Patent Atty's LLC

(57) ABSTRACT

The effectiveness of interferon for treating multiple sclerosis and other demyelinating diseases is synergistically potentiated by concomitant administration of a compound of Formula (I): wherein $R_1$ is H, alkyl or OH, $R_2$ is hydroxyalkyl or alkyl-O-$L_1$, $R_3$ is H or OH, X is C(=CH$_2$), CH(OH), or spirooxirane-2, Z is CH$_2$CH(OH) or C(=O), and $R_4$ is an optionally substituted $L_2$-alkyl or $L_2$-alkenyl, wherein $L_2$ is an optionally substituted 3-furanyl or 3-fur-3-enyl moiety.

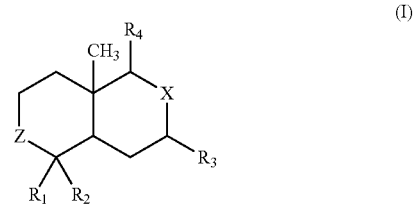

(I)

19 Claims, 9 Drawing Sheets

Figure 7
Disease progression Tratamiento IFNbeta
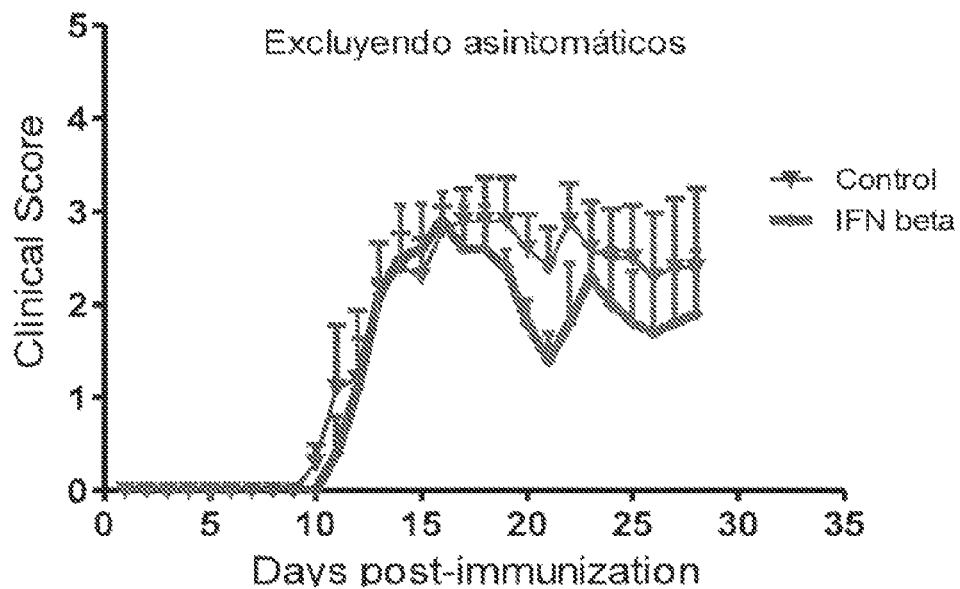
Disease progression Tratamiento Andrografólido
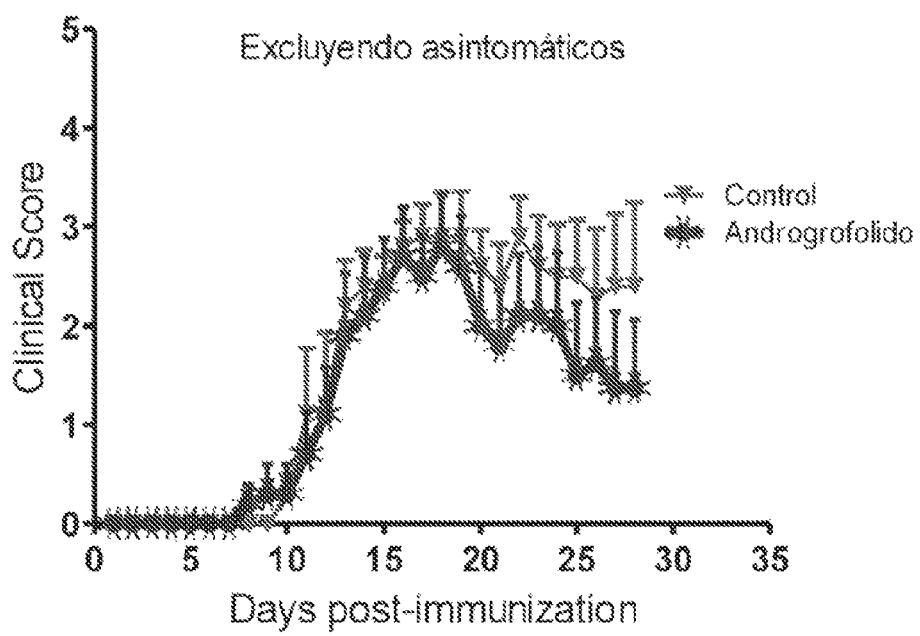

Figure 8
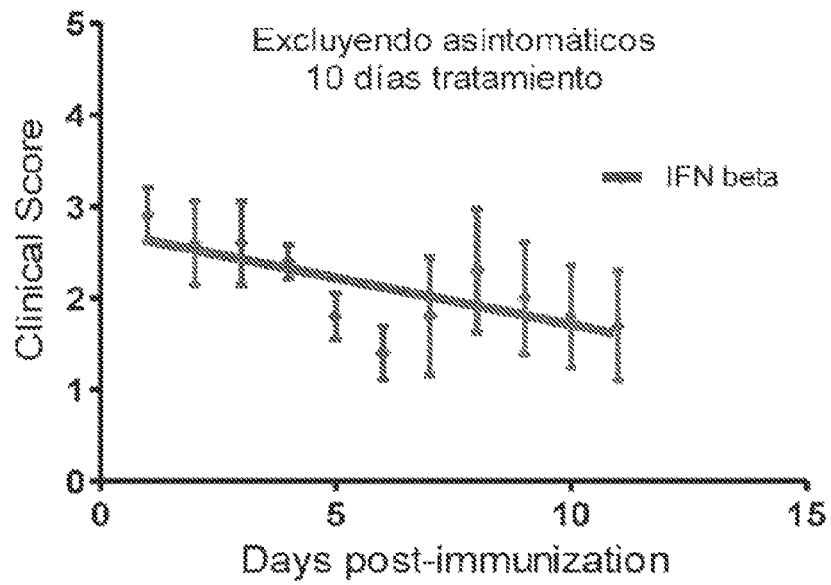
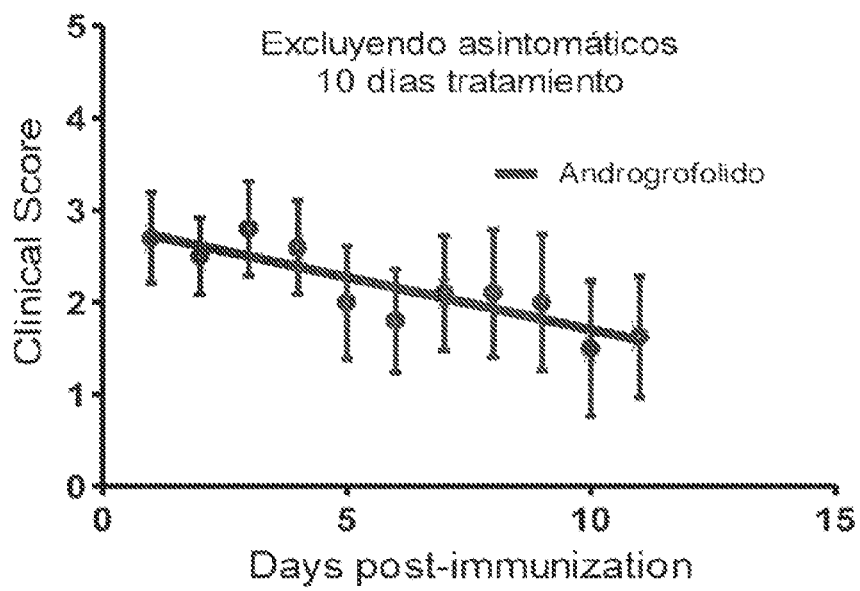

COMBINATION THERAPY WITH INTERFERON AND ANDROGRAPHOLIDES FOR MULTIPLE SCLEROSIS

The instant application is a National Stage entry of International Application No. PCT/US2012/70568 filed on 19 Dec. 2012, which claims priority from U.S. Provisional patent application No. 61/578,650 filed on 21 Dec. 2011, the contents of which are hereby incorporated by reference.

FIELD OF THE INVENTION

The present invention relates to pharmaceutical compositions for treating Multiple Sclerosis (MS) and/or other demyelinating diseases, comprising an interferon (IFN), compound of Formula I, and, optionally, one or more pharmaceutically acceptable excipients and/or carriers. Another object of the present invention is to provide a method for treating a subject suffering from MS and/or another demyelinating disease, and a method for reducing fatigue in a subject in need thereof.

BACKGROUND OF THE INVENTION

Multiple Sclerosis (MS) is a chronic, inflammatory, demyelinating disease of the Central Nervous System (CNS). It starts typically between 20 and 40 years of age, and prevails over women. MS is clinically definite diagnosed after at least two neurologic events, showing demyelination in different areas of the CNS and in different times (Jacobs et al. 2000, The New England Journal of Medicine. 343(13): 898-904).

The cause of MS is still unknown, but several lines of evidence, derived from the experimental autoimmune encephalomyelitis, support the autoimmune origin of the disease (Inglese et al. 2010, NMR Biomed. 23(7): 865-872). MS is characterized by areas of demyelinated plaques or islands disseminated throughout the CNS with a predilection for optic nerves, spinal cord, periventricular white matter (WM), corpus callosum, and cortical and sub-cortical gray matter (GM). (Inglese et al. 2010, NMR Biomed. 23(7): 865-872). Lesions in MS are very heterogeneous, respect to the presence and extend of inflammation, demyelination, axonal injury, gliosis and remyelination (Inglese et al. 2010, NMR Biomed. 23(7): 865-872).

Functional Systems Scores (FSS) and Expanded Disability Status Scale (EDSS) constitute one of the oldest and most widely utilized assessment instruments in MS (Kurtzke J. F. 1983, Neurology, 33:1444-1452). Based on a standard neurological examination, the 7 functional systems are rated. These ratings are then used in conjunction with observations and information concerning gait and use of assistive devices to rate the EDSS. Each of the FSS is an ordinal clinical rating scale ranging from 0 to 5 or 6. The EDSS is an ordinal clinical rating scale ranging from 0 (normal neurologic examination) to 10 (death due to MS) in half-point increments.

Magnetic resonance imaging (MRI) of the brain, can add certainty to the diagnosis, by identifying lesions consistent with the occurrence of demyelination.

Incorporation of IFNs to treatment of MS has opened a new pharmaceutical pathway respect to traditional immunosuppressive drug (Zaragozá et al. 2002, Farmacia Hospitalaria. 26(5): 294-301).

Interferons are cytokines with antiviral, antiproliferative, and antitumor activity, although they have different immunomodulatory characteristics. Therefore, these molecules have a great therapeutic potential in neoplastic and viral diseases. There are different types of IFNs: interferon-alpha (IFN-α), produced by leucocytes, interferon-beta (IFN-β), produced by fibroblasts and interferon-gamma (ING-γ), produced by lymphocytes-T (Zaragozá et al. 2002, Farmacia Hospitalaria. 26(5):294-301).

Particularly, several data has shown the efficiency of IFN-β in the treatment of MS. Different randomized, double-blind, placebo-controlled clinical trials has demonstrated a beneficial effect in a variety of parameters of the disease, reducing disability, frequency of relapsing, frequency of appearance of new lesions, and improving cerebral atrophy (Zaragozá et al. 2002, Farmacia Hospitalaria. 26(5): 294-301).

Despite teaching the use of IFN-β for MS, however, the art also recognizes that such treatment is only moderately effective; IFN-β at best merely slows the progression of MS, it does not cure MS. Further, the relatively high cost of IFN-β renders it financially unavailable to many patients who need it. The art thus has a long-felt need for a more effective treatment for MS.

SUMMARY

Our results show that the treatment of MS and other demyelinating diseases using an IFN is surprisingly improved if the IFN is administered together with a compound of Formula I:

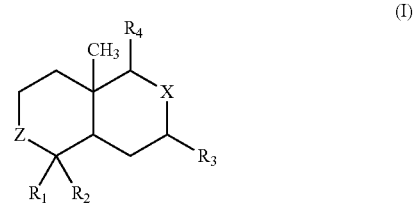

(I)

wherein $R_1$ is selected from the group consisting of hydrogen, alkyl or hydroxyl, $R_2$ is selected from the group consisting of hydroxyalkyl or alkyl-O-$L_1$, wherein $L_1$ is a carbohydrate moiety, $R_3$ is selected from the group consisting of hydrogen or hydroxyl, X is selected from the group consisting of C(=$CH_2$), CH(OH), or a spirooxirane-2 moiety (i.e., an epoxidated C(=$CH_2$) moiety,

Z is selected from the group consisting of $CH_2$, CH(OH) or C(=O), and $R_4$ is selected from the group consisting of an optionally substituted $L_2$-alkyl or $L_2$-alkenyl, wherein $L_2$ is an optionally substituted 3-furanyl or 3-fur-3-enyl moiety. The Formula I compound may be provided as a pharmaceutically acceptable salt, ester, ether or pro-drug thereof; and optionally may be formulated into a finished oral dosage form using one or more pharmaceutically acceptable excipients and/or carriers.

We have found this combination both favors remyelination and reduces inflammation and fatigue, thus achieving a synergistic effect. We have demonstrated that the administration of compound of Formula I in combination with IFN-beta reduces significantly the clinical signs of MS; a synergistic effect of the two active ingredients.

There are examples of combination of interferon and other substances for preparation of compositions for treating different diseases. Document US2009/0280087, for example, discloses the combination of Interferon alpha and C-Phycocianin for a pharmaceutical preparation for autoimmune disease, allergy and cancer treatments. Document U.S. Pat. No. 6,869,600 discloses the use of growth hormone (GH) together with an interferon (IFN) to produce a pharmaceutical composition for treating multiple sclerosis and/or other demyelinating diseases. The prior art, however, fails to suggest combining interferon with any compound of Formula I.

Therefore, a main object of the present invention is to provide pharmaceutical compositions for treating Multiple Sclerosis (MS) and/or other demyelinating diseases, comprising an interferon (IFN), compound of Formula I, and, optionally, one or more pharmaceutically acceptable excipients and/or carriers.

Another object of the present invention is, therefore, to provide a method for treating a subject suffering from MS and/or another demyelinating disease, the method consisting of administering the pharmaceutical compositions of the invention to the subject in an effective amount and for a time sufficient to produce remyelination and to reduce inflammation.

Also another object of the invention is to provide a method to reduce fatigue in a subject in need thereof; the method consisting of administering the pharmaceutical compositions of the invention to the subject in an effective amount and for a sufficient time.

DETAILED DESCRIPTION

The present invention provides pharmaceutical compositions and methods for treating Multiple Sclerosis (MS) and/or other demyelinating diseases, comprising combination therapy with an interferon (IFN) and at least one compound of the Formula (I):

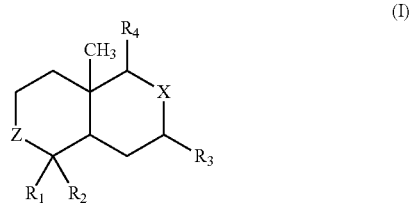

(I)

wherein
$R_1$ is selected from the group consisting of hydrogen, alkyl or hydroxyl,
$R_2$ is selected from the group consisting of hydroxyalkyl or alkyl-O-$L_1$, wherein $L_1$ is a carbohydrate moiety,
$R_3$ is selected from the group consisting of hydrogen or hydroxyl,
X is selected from the group consisting of C(=$CH_2$), CH(OH), or a spirooxirane-2 moiety.
Z is selected from the group consisting of $CH_2$, CH(OH) or C(=O), and
$R_4$ is selected from the group consisting of an optionally substituted $L_2$-alkyl or $L_2$-alkenyl, wherein $L_2$ is an optionally substituted 3-furanyl or 3-fur-3-enyl moiety, or a pharmaceutically acceptable salt, ester, ether or prodrug thereof, and, optionally, one or more pharmaceutically acceptable excipients and/or carriers. By "spirooxirane-2 moiety" we mean an epoxidated C(=$CH_2$) moiety:

In one embodiment, $R_1$ is methyl.
In another embodiment, $R_2$ is hydroxymethyl or $CH_2$—O—Glc, wherein Glc is a glycoside-forming glucose moiety.
In another embodiment, $R_4$ is an optionally substituted 3-(3-furanyl)-propyl, 3-(3-furanyl)-prop-1-enyl, 3-(3-furanyl)-prop-2-enyl, 3-(3-fur-3-enyl)-propyl or 3-(3-fur-3-enyl)-prop-1-enyl wherein the 3-furanyl or the 3-fur-3-enyl moieties are further optionally substituted.

In one embodiment, $R_1$, $R_2$, $R_3$, X and Z are those described above, and $R_4$ is selected from the group consisting of:

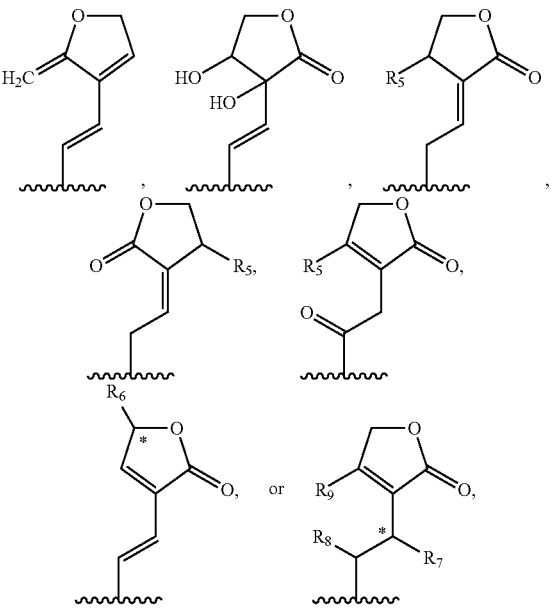

wherein:
$R_5$ is selected from the group consisting of hydrogen or hydroxyl,
$R_6$ and $R_7$ are independently selected from the group consisting of hydrogen, hydroxyl, or alkyloxy, or $R_6$ and $R_7$ are simultaneously replaced by a single direct bond between the carbon atoms denoted by *, thus forming a dimer of two monomer molecules of formula (I), and $R_8$ and $R_9$ are independently selected from the group consisting of hydrogen, hydroxyl or alkyloxy.

In one embodiment, $R_6$, $R_7$, $R_8$ or $R_9$ can be independently methoxy.

In preferred embodiments, the compounds of Formula (I) are selected from the group consisting of andrographolide, neoandrographolide, 14-deoxyandrographolide 14-deoxy-11,12-didehydroandrographolide, andrographiside, andrograpanin, 14-deoxy-11-oxoandrographolide, 14-deoxy-11-hydroxy-andrographolide, 14-deoxy-12-hydroxy-andrographolide, 3,14-dideoxyandrographolide, 3-oxo-14-deoxyandrographolide, 8,17-epoxy-14-deoxyandrographolide, 14-deoxy-17-beta-hydroxyandrographolide, 12-hydroxyandrographolide, bisandrographolide A, 3-oxo-14-deoxy-11,12-didehydroandrographolide, 7-hydroxy-14-deoxyandrographolide, 15-methoxy-3,19-dihydroxy-8(17) 11,13-ent-labda-trien-16,15-olide, andropanolide, 14-deoxy-12-methoxy-andrographolide, 14-epi-andrographolide, 19-hydroxi-ent-labda-8(17), 13-dien-15,16-olide, 3,13,14,19-tetrahydroxy-ent-labda-8(17), 11-dien-16,15-olide, 3,19-dihydroxy-15-methoxy-ent-labda-8(17), 11,13-trien-16,15-olide, and 3,19-dihydroxy-ent-labda-8(17), 12-dien-16,15-olide.

In a most preferred embodiment, the compound of formula I comprises andrographolide. Andrographolide, CAS Registry No. 5508-58-7, systematic name 3-(2-(Decahydro-6-hydroxy-5-(hydroxymethyl)-5,8a-dimethyl-2-methylenenaphthyl)ethylidene)dihydro-4-hydroxyfuran-2(3H)-one, is a compound of Formula I, wherein R1 is alkyl, R2 is hydroxyalkyl, R3 is H, X is C=CH2, Z is CH(OH) and R4 is an (E)-4-hydroxy-3-propylidenedihydrofuran-2(3H)-one moiety:

Andrographolide is a bitter principle, colorless, neutral crystalline substance, is a diterpene containing a γ-lactone ring. The crystal structure of andrographolide was determined by Smith et al (1982) and Fujita et al (1984). Andrographolide can be isolated from the aerial part of *Andrographis paniculata* by extraction with alcohol or with alkaline solutions. Hydrolysis of andrographolide under cleavage of the lactone ring yields salts of andrographolic acid which can be reconverted into andrographolide by acidification (Tang and Eisenbrand 1992).

In another most preferred embodiment, the compound of formula I comprises neoandrographolide. Neoandrographolide, CAS Registry No. 27215-14-1, systematic name 3-(2-(5-((beta-D-glucopyranosyloxy)methyl)decahydro-5, 8a-dimethyl-2-methylene-1-naphthalenyl)ethyl)-(1R-(1alpha,4abeta,5alpha,8aalpha))-2(5H)-furanone, was first described by Kleipool (Kleipool, 1952).

The structure of neoandrographolide was described as a diterpene glucoside (Chan et al., 1971).

In another most preferred embodiment, the compound of Formula I comprises deoxy-didehydroandrographolide, deoxy-oxoandrographolide or deoxyandrographolide, each structurally closely related to andrographolide. See Bailmain and Connolly (1973).

In another most preferred embodiment, the compound of Formula I comprises dideoxyandrographolide (also referred to as andrograpanin, see Fujita et al., (1984)), andrographiside or a 14-deoxy derivative thereof (e.g., 14-deoxyandrographiside).

Dideoxyandrographolide is the aglicone of neoandrographolide.

Jantan and Waterman (1994) isolated from the aerial part of a Malaysian specimen other diterpene as the principle constituents, indicating that *A. paniculata* presents great variation in chemical compositions depending on the source of origin (Jantan et al., 1994).

In another most preferred embodiment, the compound of Formula I comprises 3-O-β-D-glucopyranosyl-14,19-dideoxyandrographolide, 14-deoxy-17-hydroxyandrographolide, 19-O-[β-D-apiofuranosyl(1f2)-β-D-glucopyranoyl]-3,14-dideoxyandrographolide, 3-O-β-D-glucopyranosylandrographolide, 12S-hydroxyandrographolide and/or andrographatoside. The structures of each are taught by Shen et al. 2006.

In another most preferred embodiment, the compound of Formula I comprises andropanolide or isoandrographolide. The structures of each are taught by Pramanick et al., 2006.

The prior art teaches that andrographolide reduces interferon gamma production. See Burgos et al., 2005, U.S. Pat. No. 8,084,495 (andrographolide reduces production of interferon γ in T-cells stimulated with concanavalin A). Because the prior art taught that andrographolide reduces interferon production, the skilled artisan would have predicted that andrographolide (or similar compounds of Formula I) would have been detrimental if administered to a patient suffering from a condition (such as multiple sclerosis) which is known to be treated by administering exogenous interferon. Rather, the artisan would have predicted that compounds of Formula I would be at best ineffective, and at worst actively reduce the efficacy of exogenous interferon.

In testing this hypothesis in laboratory mice, however, we surprisingly found the direct opposite of what one would have expected: we found that concomitant administration of a compound of Formula I increases the effectiveness of interferon, producing an unexpected and synergistic improvement in health status.

Without intending to limit the legal scope of the legal claims of the instant patent, we believe that this synergistic effect may be explained by the following mechanism: we (and others) have described that andrographolide can interfere with the Nuclear factor kappaB (NF-κB) binding to DNA (Hidalgo et al., 2005; Xia et al., 2004b) (U.S. Pat. No. 8,084, 495). NF-κB is a transcription factor found in a great variety of immune cells, participating in the regulation of genes involved in cellular and physiological processes, such as growth and apoptosis, and it has an important role in inflammatory and immune responses, by inducing transcription of pro inflammatory genes (Baeuerle et al., 1996). For instance, the pro inflammatory mediators such as intercellular adhesion molecule-1, IFNγ, iNOS, COX-2 and IL-8 are proteins regulated by NF-κB. Since andrographolide is able to down-modulate both, humoral and cellular adaptive immune responses, we suspect this evidence may support an immune-suppressant effect.

It has been demonstrated in vitro, that this molecule is able to interfere with T cell proliferation and cytokine release in response to allogenic stimulation. The T cell activation by dendritic cells (DCs) was completely abolished by exposing DCs to andrographolide during antigen pulse (Iruretagoyena et al., 2005). Andrographolide is able to interfere with maturation of DCs and with their ability to present antigens to T cells.

We also found that andrographolide can interfere with cytokine production in Jurkat cells. This effect can be mediated by a reduction of IL-2 production by a reduction of signal transduction pathways and/or interference with transcription factors activation. We proposed that the cytokine inhibition by andrographolide, can be produced by an interference with ERK1/2, a MAPK involved in IL-2 and IFNγ production in T-cells (Burgos et al., 2005). Other authors showed that andrographolide in dose-dependent manner inhibited macrophages migration toward C5a. The chemotaxis inhibition is explained because andrographolide significantly attenuated C5a-stimulated phosphorylation of ERK1/2, and of its upstream activator, MAP kinase-ERK kinase (MEK1/2) and Akt phosphorylation, a downstream target protein for PI3K (Tsai et al., 2004). The interference of ERK1/2 phosphorylation also explains the inhibitory effect of andrographolide on TNF-alpha, IL-12a and IL-12b at mRNA level, and production of TNF-alpha and IL-12p70 proteins in a concentration-dependent manner in murine macrophages (Qin et al., 2006). An interference of signal transduction pathways in T-cells has been recently observed. Using anti-CD3 or PMA/Iono we demonstrated that andrographolide can reduce phosphorylation of ERK1/2 and ERK5. These pathways are responsible for cytokine production (Dumont et al., 1998; Garaude et al., 2005), however, a key step is the activation of the Nuclear factor in activated T cells (NAFT), which is one of the major transcription factors binding to IL-2 gene promoters.

We demonstrated using NFAT-luc that andrographolide can interfere with NFAT activation, probably by a reduction of translocation to the nucleus, thus explaining the decrease of IL-2 production.

Furthermore, in vivo immune responses such as antibody response to a thymus-dependent antigen and delayed-type hypersensitivity is drastically diminished in mice by andrographolide treatment. The andrographolide inhibition of T cells, was applied to interfere with the onset of experimental autoimmune encephalomyelitis (EAE), an inflammatory demyelinating disease of the central nervous system that is primarily mediated by CD4 (+) T cells, which serves as an animal model for human Multiple Sclerosis. Treatment with andrographolide was able to significantly reduce EAE symptoms in mice by inhibiting T cell and antibody responses directed to myelin antigens (Iruretagoyena et al., 2005).

Using a MOG-induced (myelin-oligodendrocyte-glycoprotein induced) EAE mice model, we found that daily treatment with 2 mg/kg s.c. of andrographolide produced an important improvement in clinical scores of animals treated with andrographolide compared with animals treated with saline. Similarly, in another model of autoimmune disease, the administration of andrographolide reduced the susceptibility, prevented the symptoms and reduced anti-nuclear antibodies and kidney damage of systemic lupus erythematous.

A synergistic effect of andrographolide treatment and IFN-β on the mice model of EAE was shown. Mean clinical scores of mice injected with IFN-β showed a mild decrease in mean clinical scores compared with saline injected controls. However, when combined with andrographolide, the IFN-β treatment showed a more significant reduction in the mean clinical scores. Our results show a clear beneficial effect of andrographolide on IFN-β treatment, when administered during the active phase of the disease (day 16-31), which reduces clinical signs of chronic EAE in mice after immunization with MOG. Androgrpaholides potentiate the effect of interferon beta and therefore is a therapeutic tool from MS and demyelinating diseases stronger than interferon beta alone.

Because andrographolide can modulate several transcription factors or signaling pathways, involving inflammatory processes and activation of T-cells, andrographolide together with IFN formulations could be a useful therapy for MS.

DEFINITIONS

An "effective amount" refers to an amount of the active ingredients that is sufficient to affect the course and the severity of the disease, leading to the reduction or remission of such pathology. The effective amount can be readily determined by a person skilled in the art and will depend on the route of administration, the weight, the age and the condition of the patient, and the goal of the administration (therapeutic, prophylactic or diagnostic goal).

The term "interferon", as used in the present patent application, is intended to include any molecule defined as such in the literature, comprising for example any kinds of IFNs mentioned in the above section "Background of the Invention". In particular, any kinds of IFN-alpha, IFN-beta and IFN-gamma are included in the above definition. IFN-beta is the preferred IFN according to the present invention.

The pharmaceutical compositions of the present invention can comprise naturally occurring, native, mutant, synthetic or recombinant IFNs.

The term "interferon-beta (IFN-beta)", as used herein, includes human fibroblast interferon, as obtained by isolation from biological samples or as obtained by recombinant DNA techniques from prokaryotic or eukaryotic host cells as well as its salts, functional derivatives, variants, analogs and fragments.

"Derivatives" as used herein covers derivatives which may be any purified compound, comprising preferably from 90 to 100% of the pure compound, and any compound of Formula I. Standardized compositions obtained from *A. paniculata*, containing high concentrations of compound of Formula I can also be considered as compound(s) of Formula I as used in the present invention.

The compounds of Formula I are preferably prepared as purified compounds, comprising preferably at least about 90% of the pure compound, more preferably at least about 98% of the pure compound. An adequate diluent can also be used, allowing the reconstitution of the product to the desired concentration prior to administration of the dose. The compounds of Formula I can be prepared as pharmaceutical finished dosage forms any known manner, such as a pre-filled syringe, etc.

The pharmaceutical compositions of the invention can comprise purified compounds of Formula I and/or a mixture of compounds of Formula I. The aforementioned mixture of compound(s) of Formula I can be synthetically blended or naturally occurring.

"Pharmaceutically acceptable diluents, stabilizers, buffers, preservatives, solubilizers, emulsifiers, adjuvants and/or carriers" as use herein, is meant that those compounds do not interfere with the biological activity of the active ingredients and are not toxic to the host to which is administrated.

In a preferred embodiment a pharmaceutical composition of the invention comprise between 6 and 12 MUI of IFN-beta, and between 50 and 500 mg of compound of Formula I. In a more preferred embodiment, a pharmaceutical composition of the invention comprise between 6 and 12 MUI of IFN-beta, and between 100 and 200 mg of compound of Formula I.

The administration of the pharmaceutical compositions of the present invention may be by intravenous, intramuscular, subcutaneous, or oral route, or any other route which may establish the desired blood levels of the active compounds. For example, for parenteral administration, the pharmaceutical compositions of the present invention may be formulated as unit dosage form for injection in vehicles such as sterile water, saline, dextrose solution, serum albumin and/or Ringer's solution.

The pharmaceutical compositions of the invention are suitable for treating MS and/or other demyelinating diseases.

The pharmaceutical compositions of the invention are designed for the simultaneous, separate or sequential use of its active ingredients for the above specified therapy.

The present invention provides a method for treating a subject suffering from MS and/or another demyelinating disease, the method consisting of administering a pharmaceutical composition of the invention to the subject in an effective amount, intravenously, intramuscularly, subcutaneously, or orally every day or every other day and for time sufficient to produce remyelination and to reduce inflammation. In a preferred embodiment, the effective amount of the pharmaceutical composition comprises between 6 and 12 MUI of IFN-beta and between 1 and 5 mg/Kg body weight of compound of Formula I. In a more preferred embodiment, the effective amount of the pharmaceutical composition comprises between 6 and 12 MUI of IFN-beta and 2 mg/Kg body weight of compound of Formula I. In a preferred embodiment, the administration of the pharmaceutical composition is for an unlimited time.

The present invention also provides a method to reduce fatigue in a subject in need thereof, the method consisting of administering the pharmaceutical compositions of the invention to the subject in an effective amount every day or every other day. In a preferred embodiment, the effective amount of the pharmaceutical composition comprises between 6 and 12 MUI of IFN-beta and between 1 and 5 mg/Kg body weight of compound of Formula I. In a more preferred embodiment, the effective amount of the pharmaceutical composition comprises between 6 and 12 MUI of IFN-beta and 2 mg/Kg body weight of compound of Formula I. In a preferred embodiment, the administration of the pharmaceutical composition is for an unlimited time. The present invention has been described with reference to the preferred embodiments, but the content of the description comprises all modifications and substitutions which can be brought by a person skilled in the art without extending beyond the meaning and purpose of the claims.

BRIEF DESCRIPTION OF THE DRAWINGS

FIG. 7 measures disease progression (excluding asymptomatic subjects) with IFNbeta treatment and with andrographolide treatment.

FIG. 8 measures disease progression (excluding asymptomatic subjects) with IFNbeta treatment and with andrographolide treatment.

EXAMPLES

Figure 1:
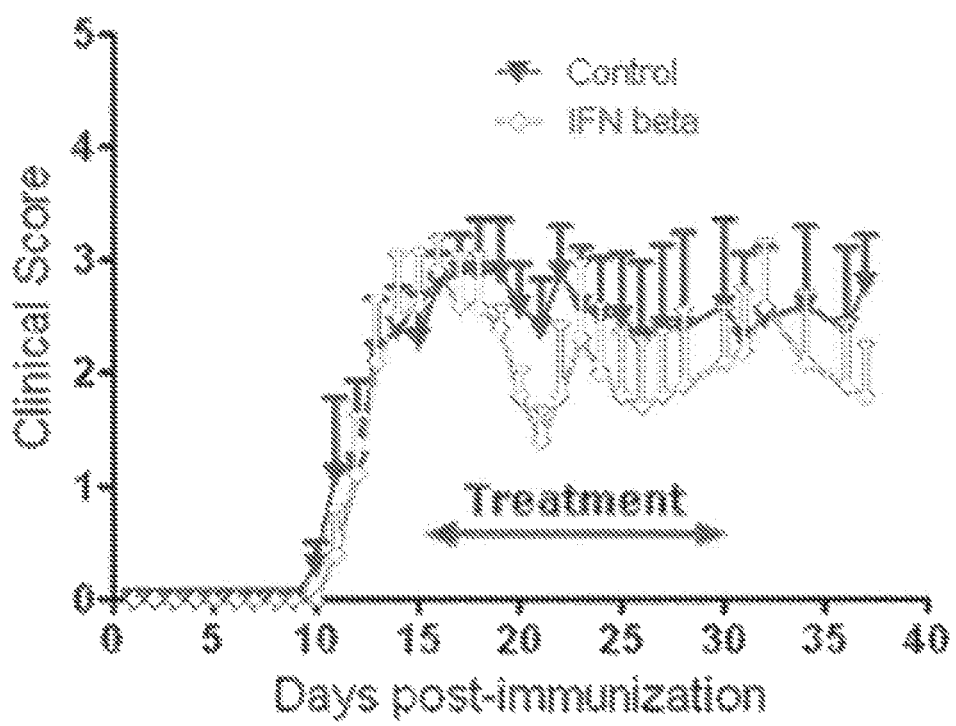
FIG. 1: Effect of IFN-β on disease severity in EAE mice. Mice were treated daily with IFN-β (1 μg of IFN-β in 200 μL PBS, ip), at the beginning of chronic phase (day 15 post-immunization) until day 30 post-immunization. As controls MOG-immunized C57BL/6J mice were injected with PBS (Vehicle).

The following examples illustrate the invention in detail, but they are not intended to limit the scope of the invention.

Example 1

Mice with Induced Experimental Autoimmune Encephalomyelitis (EAE) Administered with Combined Therapy of Andrographolide and Interferon Animals C57BL/6 mice were purchased from Jax® mice laboratories and housed at Pontificia Universidad Catolicas animal facility. Animal care and use was performed in accordance with approved animal use protocols and guidelines of Institutional Animal Care and Use Committee.

Experimental Autoimmune Encephalomyelitis (EAE) Induction and Treatments

EAE was induced by immunization with myelin oligodendrocyte glycoprotein (MOG)35-55 peptide (MEVGWYR-SPFSRVVHLYR) or proteolipid protein (PLP)139-151 (HSLGKWLGHPDKF; CPC Scientific, Sunnyvale, Calif., USA) emulsified at 1.5 mg/ml in PBS with an equal amount of incomplete Freund's adjuvant (IFA; DIFCO, MI, USA) supplemented with 2.5 mg/ml *Mycobacterium tuberculosis*, strain H37Ra (Difco, Detroit, Mich.). Mice were immunized subcutaneously with 200 ml emulsion. Pertussis toxin (LIST BIOLOGICAL LABS, CA, USA), 200 ng in 200 μl PBS, was injected intraperitoneally at day 0 and 2 after initial immunization.

Animals were scored for clinical symptoms as follows: 0=no signs of disease; 1=lost of tail tone; 2=flaccid tail; 3=partial hind limb paralysis; 4=complete hind limb paralysis; 5=moribund required to sacrifice the animal; 6=death.

For IFN-β assays, C57BL/6, were administered intraperitoneally with 1 μg of IFN-β (IFN-β Rebif 88 μ/ml MERCK SORONO) in 200 μL PBS. Control mice were injected with 200 μL PBS.

IFN-β was administrated from day 15 to 30 post-immunization, daily.

For combined therapy (CT) assays, C57BL/6, were administered intraperitoneally with 4 mg/kg of andrographolide and IFN-β 1 ug in 200 μL PBS. Control mice were injected with 200 μL PBS.

Combined therapy (CT) was administrated from day 15 to 30 post-immunization, either daily or every second day. At day 36 all animals were sacrificed. Clinical score was registered, and spinal cords were collected for histological analysis.

Histological Preparation

Mice were deeply anesthetized with isoflurane and perfused transcardially with ice-cold 1×PBS (25 ml), followed by 4% p-formaldehyde. Spinal cords were dissected and post-fixed in 4% PFA overnight at 4° C. Tissue was cryoprotected in 30% (w/v) sucrose at 4° C. overnight, embedded in OCT compound, frozen and sectioning with a cryostat at 20 μm thick.

Spinal Cord Inflammatory Infiltrate

To evaluate inflammatory infiltrate, hematoxylin eosin staining (H&E) was performed. Toraxic spinal cord sections were stained with hematoxylin solution modified to Gill (SIGMA, USA), and with eosin Y (SIGMA, USA). Mononuclear cell infiltration was determined as the area occupied by positive nuclei in the spinal cord periphery of 4 different sections.

Spinal Cord Myelin Staining

To evaluate demyelination in EAE spinal cord, luxol fast blue (LFB) staining was performed. Toraxic spinal cord sections were stained with LFB (SIGMA, USA), and neuron nuclei were staining with cresyl violet. Demyelination was evaluated as LFB staining free area in spinal cord white matter.

Immunohistochemistry

Sections of the spinal cord (20 mm) were treated with a permeabilization/blocking solution containing 10% FCS, 1% glycine, and 0.05% Triton X-100 (Sigma-Aldrich). Primary antibody rat anti CD11b (1:200; BD, USA) in blocking solution was applied O.N. in a humidified chamber at 4° C. Secondary antibody goat anti rat conjugated with fluorescein (Millipore, USA) was applied for 1 h at room temperature.

Figure 2:
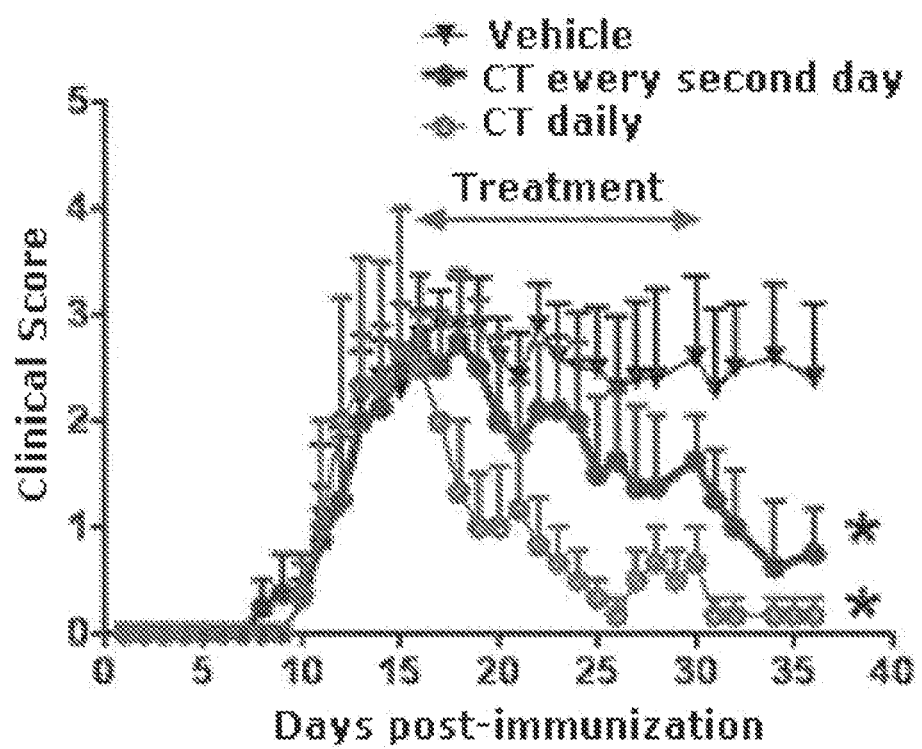
FIG. 2: Effect of combined therapy on disease severity in EAE mice. This figure shows two groups of MOG-immunized C57BL/6J mice (150 ug MOG-peptide; 500 ug MT; 200 ng PT) treated daily, or every second day with the combined therapy (4 mg/kg andrographolide and 1 ug IFN-β at the beginning of chronic phase (day 15 post-immunization) until day 30 post-immunization. As controls MOG-immunized C57BL/6J mice were injected with PBS (Vehicle).

Disease Severity in IFN-β (FIG. 1) and Combined Therapy (CT) EAE Mice (FIG. 2)

Three groups of MOG-immunized C57BL/6J mice (150 ug MOG-peptide; 500 ug MT; 200 ng PT) were treated daily with IFN-β (1 μg of IFN-β (IFN-β Rebif 88 μ/ml MERCK SORONO) in 200 μL PBS, intraperitoneally), daily or every second day with the combined therapy (CT) (4 mg/kg andrographolide plus IFN-β 1 ug) at the beginning of chronic phase (day 15 post-immunization) until day 30 post-immunization. As controls MOG-immunized C57BL/6J mice were injected with PBS (Vehicle). At day 36 p.i. all mice were sacrificed (scores: PBS=2.4; CT daily=0.17; CT every second day=0.75) and processed for histological analysis.

Combined therapy decreases significantly clinical symptoms in Chronic EAE mouse model. Comparing FIGS. 1 and 2, it is demonstrated, that the addition of compound of Formula I causes a synergic effect with interferon.

Figure 3:
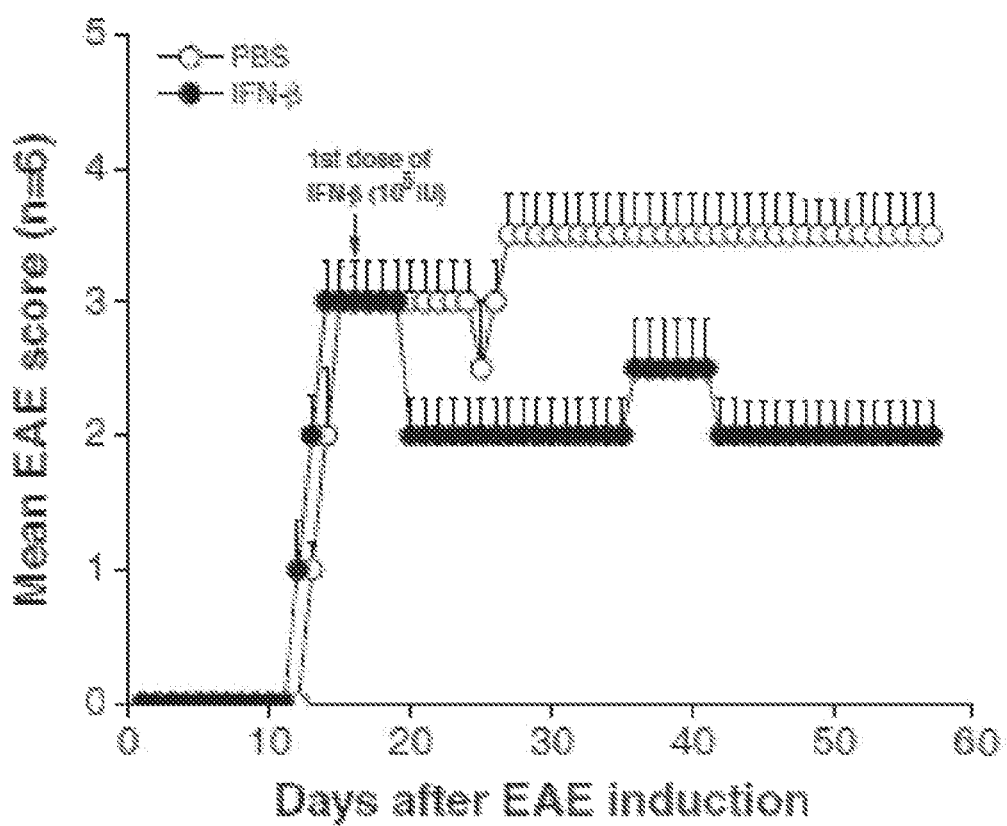
FIG. 3: The mean score for n=6 test subjects for the data shown in FIG. 1/9.

Inflammatory Infiltrate is Reduced in Spinal Cord with Combined Therapy in EAE Treated Mice (FIG. 3)

Non-immunized mice (NI) (left panel), MOG-immunized mice treated with either PBS (middle panel) or combined therapy (CT) (right panel) were perfused and 4% p-formaldehyde fixed. Spinal cords were dissected and analyzed for inflammatory infiltrate by hematoxylin-eosin staining. Insets show higher magnification (10×). Mononuclear area fraction was quantified in thoracic spinal cord using 4 different sections separated by 250 μm. Results are shown as mean±SEM.

Result:

Combined therapy decreases spinal cord cell infiltration in chronic EAE mouse model.

Figure 4:
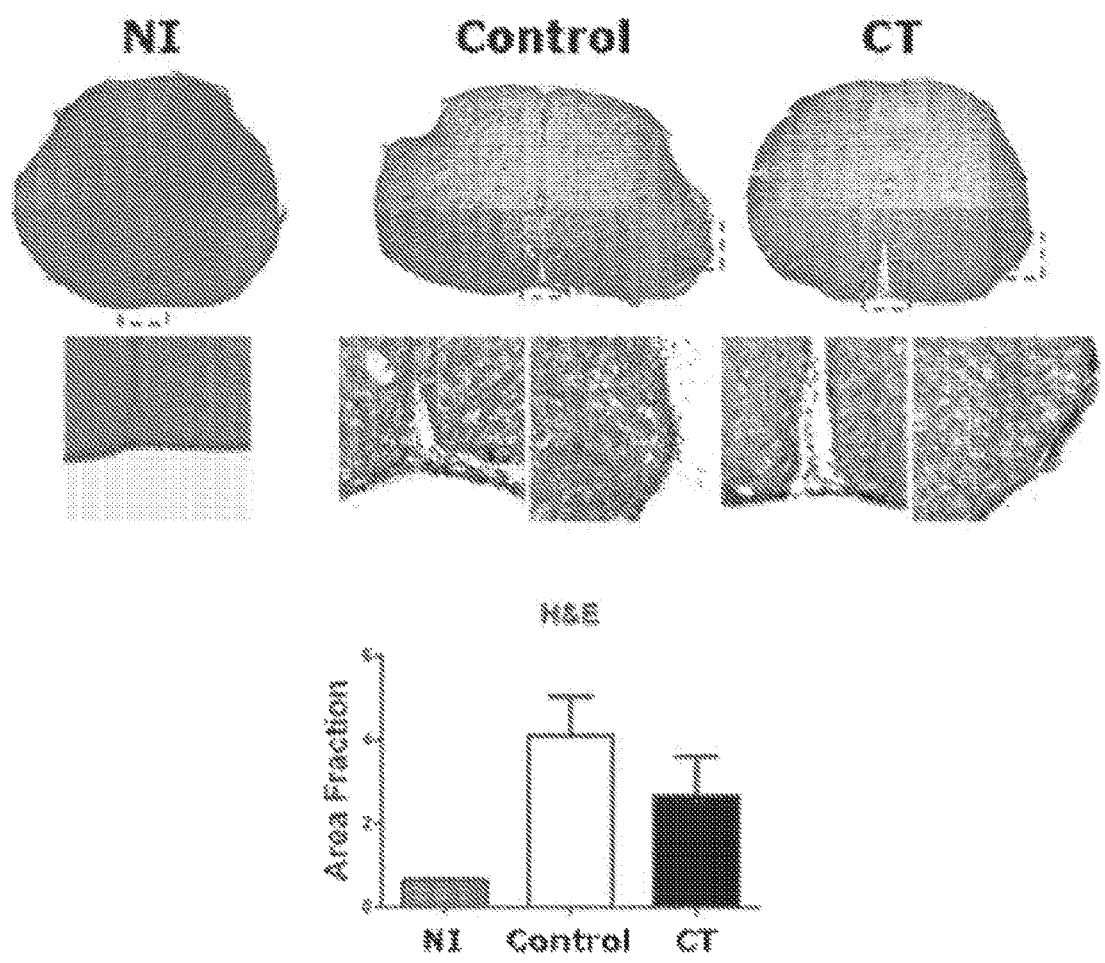
FIG. 4: Inflammatory infiltrate is reduced in spinal cord with combined therapy in EAE treated mice. Non-immunized mice (NI) (left panel), MOG-immunized mice treated with either PBS (middle panel) or combined therapy (CT) EAE treated mice (right panel) were perfused and 4% p-formaldehyde fixed. Spinal cords were dissected and analyzed for inflammatory infiltrate by hematoxylin-eosin staining. Insets show higher magnification (10×). Mononuclear area fraction was quantified in thoracic spinal cord using 4 different sections separated by 250 μm. Results are shown as mean±SEM.

Inflammatory Infiltrate and Demyelination is Reduced in Spinal Cord with Combined Therapy in EAE Treated Mice (FIG. 4).

Non-immunized mice (NI) (left panel), MOG-immunized mice treated with either PBS (middle panel) combined therapy (CT) (right panel) were perfused and 4% p-formaldehyde fixed. Spinal cords were dissected and analyzed for inflammatory infiltrate by hematoxylin-eosin staining (H&E) and demyelination was evaluated by luxol fast blue (LFB) staining. Insets show higher magnification (10×). A shows representative thoracic spinal cord sections. B shows magnifications of infiltrating cells and demyelination.

Result:

Combined therapy decreases spinal cord cell infiltration and demyelination in Chronic EAE mouse model.

Figure 5:
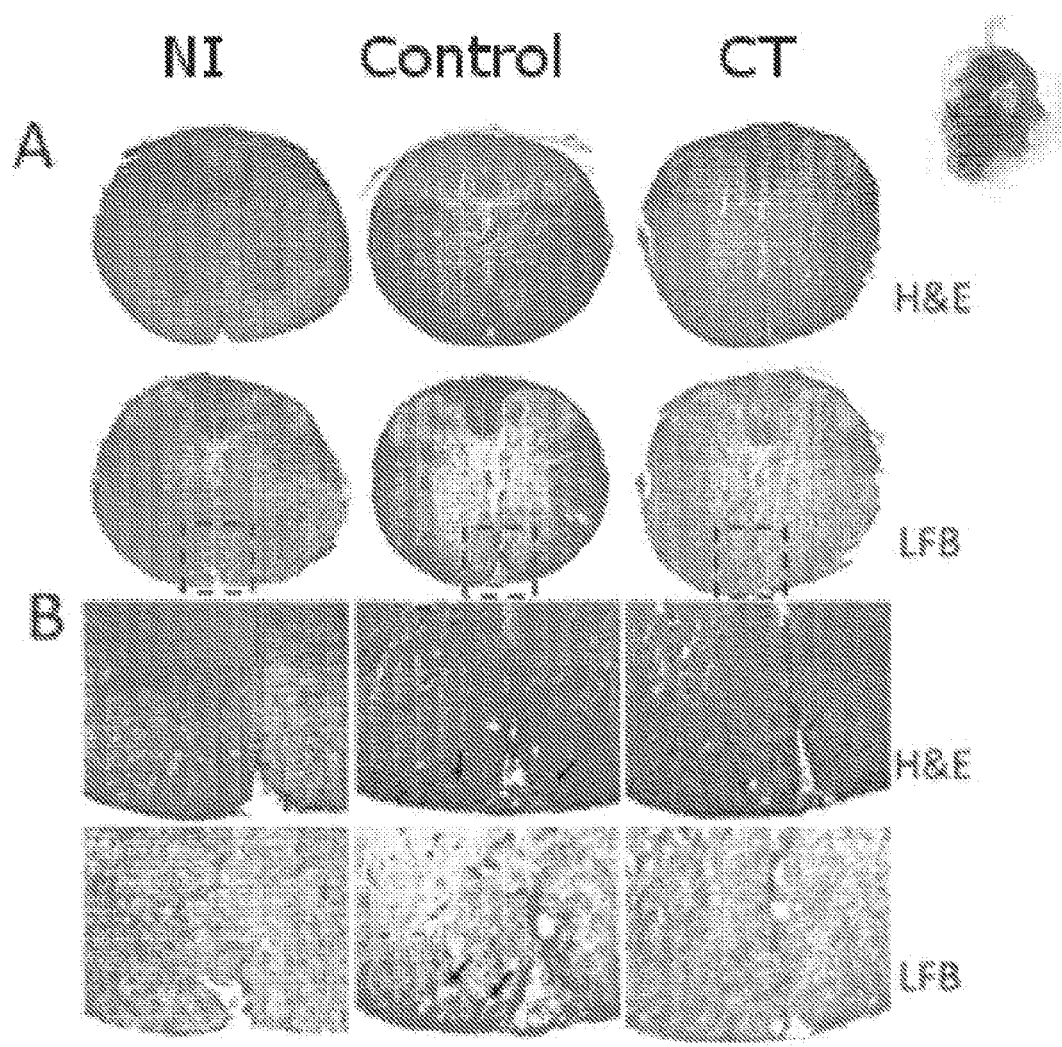
FIG. 5: Inflammatory infiltrate and demyelination is reduced in spinal cord with combined therapy in EAE treated mice. Non-immunized mice (NI) (left panel), MOG-immunized mice treated with either PBS (middle panel) or combined therapy (CT) EAE treated mice (right panel) were perfused and 4% p-formaldehyde fixed. Spinal cords were dissected and analyzed for inflammatory infiltrate by hematoxylin-eosin staining (H&E) and demyelination was evaluated by luxol fast blue (LFB) staining. Insets show higher magnification (10×). A: representative thoracic spinal cord sections. B: magnifications of infiltrating cells and demyelination.
Figure 6:
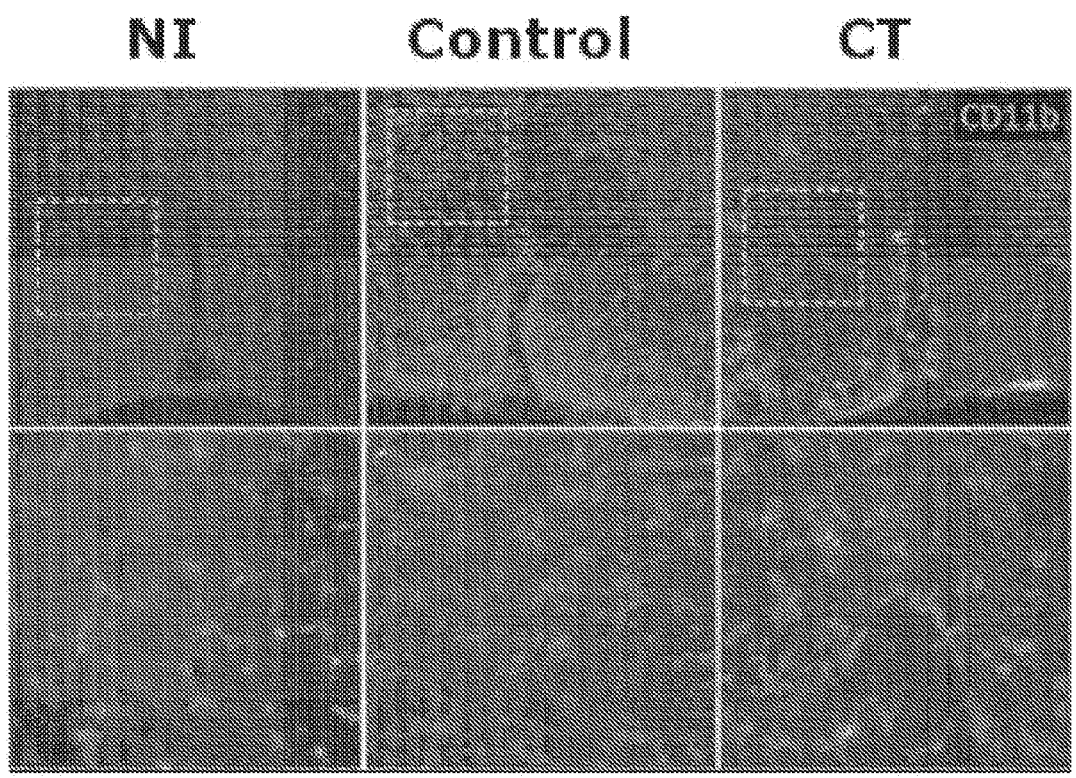
FIG. 6: Microglial cells from combined therapy (CT) EAE treated mice shows a resting phenotype. A: spinal cords from non-immunized mice (NI) (left panel), MOG-immunized mice treated with either PBS (middle panel) or combined therapy (CT) EAE treated mice (right panel) that were dissected and analyzed for macrophages/microglia by immunofluorescence using an anti-CD11b antibody followed by incubation with Alexa-fluor 488-conjugated secondary antibody (green). B: insets with higher magnification (20×).
Figure 9:
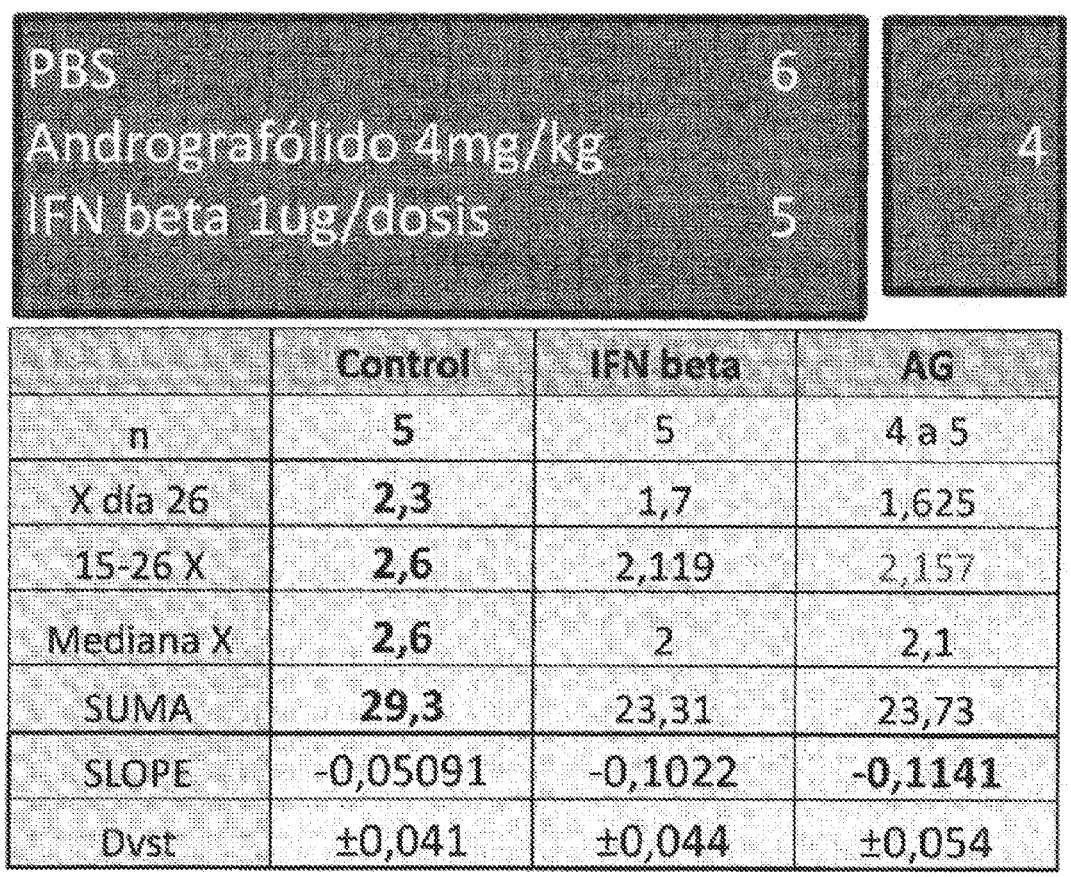
FIG. 9 measures disease progression (as the slope of the line) with PBS (control), IFNbeta treatment and AG (andrographolide) treatment.

Microglial Cells from Combined Therapy (CT) Mice Exhibited a Resting Phenotype (FIG. 5).

Panel A shows spinal cords from non-immunized mice (NI) (left panel), MOG-immunized mice treated with either PBS (middle panel) or combined therapy (CT) (right panel) that were dissected and analyzed for macrophages/microglia by immunofluorescence using an anti-CD11b antibody followed by incubation with Alexa-fluor 488-conjugated secondary antibody (green). Panel B shows insets with higher magnification (20×).

Result:

CD11b+ cells showed long processes compared to control microglial cells that exhibit short and ramified processes. Combined therapy might be preventing macrophage infiltration, microglia activation or both.

Example 2

Human Multiple Sclerosis (MS) Patients

MS Patients Receiving Andrographolide Only
Materials & Methods:
Subjects—Patients Eight MS patients were not receiving any previous regular pharmacological treatment at all, some due to clinical reasons, or economical restrictions (e.g., lack of financial access to commercially-available interferon drug products) and others or both.

Andrographolide Product

Andrographolide was obtained as a standardized extract of *Andrographis paniculata*, purified, standardized to purity and dried, commercially available from HP Ingredients, Inc., Bradenton, Fla. USA, conforming to an identity specification of ≥35.0% (w/w) of andrographolide. The material used in the testing described here had an actual identity assay of an HPLC content of 47.2% (w/w) of andrographolide, 2.1% (w/w) of neoandrografolide and 3.0% (w/w) of 14-deoxyandrografolide. (All mass measures refer to dry weight without solvent.)

Treatment Regimen

All eight patients were placed on a non-blinded, 42-month treatment regimen of daily intake (per os) at a dosage of 2 mg andrographolide per kilogram of body weight, 0.15 mg of neoandrographolide per kilogram of body weight, and 0.2 mg of deoxyandrographolide per kilogram of body weight.

Results:

Safety & Tolerability

After 42 months of treatment, no intolerance, adverse interactions or reactions to the test product have been reported or observed by any of the patients nor the attending physicians. In contrast to what is normally expected during treatment with interferon beta, none of the patients treated with andrographolide reported any flu-like side effects.

No patient showed a relapse of multiple sclerosis during the 42 months of treatment, as measured by clinical and neuroimaging controls.

All patients showed some partial functional recovery of sensitiveness and neuromotricity. In several patients, the magnitude of this recovery was clinically significant.

Clinical Results

1. All patients report some degree of symptomatic control of pain, fatigue, spasticity and improvement of mood, already noticeable at four months of therapy, but the effect was significantly less than the group receiving the Combined therapy (andrographolide combined with interferon)
2. Two patients with previously very long active disease (21 and 17 years from onset respectively) presented one early episode of relapse (within the first sixty weeks after initiated treatment), but symptoms have been very brief and mild, not requiring additional immunosuppressive treatment as they had before.
3. One patient in full clinical remission, free of symptoms or new neuroimaging lesions after more than three years, continuous only with monotherapy.
4. Partial improved focal functionality in 2 of eight patients, such as speech impairment (dysarthria) and vision at month 6; deglutition (neurologic dysphagia) and fine motricity (recovering writing, self eating and hygiene) between months 12-14.
5. One of eight patients improved scattered functionality such as fatigue, leg strength, coordination and walking equilibrium at month six, with sustained progress until now.
6. Two patients, who previous to treatment were not able to stand up or climb upstairs, have started antigravity displacement at month 30, beginning perception of initial recovery from this impairment between four and six months of monotherapy.
7. No change in the total number and size of demyelinating lesions in the brain as measured by Magnetic Resonance Imagining (MRI)
8. Some degree of reduction of inflammatory activity of demyelinating lesions comparing time 0 as measured by MRI Gadolinium contrast medium uptake and 42 months still pending).

MS Patients Receiving Interferon Beta Only

Materials & Methods:

Subjects—Patients

Ten MS patients diagnosed with Relapsing Remitting type of the disease.

Results:

Safety & Tolerability

1.—Complete safety and tolerability in all patients after 12 months (ongoing) of an interferon beta in monotherapy (either Interferon beta-1a (IFNβ-1a) Avonex® 30 μg/weekly (im), Interferon beta-1a (IFNβ-1a) Rebif® 22 μg o 44 μg/3 times a week (sc)

Interferon beta-1b (IFNβ-1b) Betaferon®/Betaseron® following the instructions of the physician Some degree of adverse reactions to the test product have been reported or observed by these patients or physicians.

2. No relapses during the 12 months of treatment, as measured by clinical and neuroimaging controls.
3. Appearance of flu-like symptoms such as aches and pains, fever, chills, sweating or headache in 6 of 8 patients some of which required the use of aspirin or ibuprofen.
4.—Two patients reported mild depression at the 4th month during treatment Clinical Results 1. All patients reported no degree of symptomatic control of fatigue and improvement of mood, as seen in the group with ANG or receiving the Combined Theraphy (ANF+INF).
2. No patients presented episodes of relapse (within the first year of treatment).
3. No patients showed clinical signs of subjective wellness, despite the fact of appearance of new neuroimaging lesions.
4. No improvement on speech impairment (dysarthria) and vision nor deglutition (neurologic dysphagia) and fine motricity.
5. No effect on antigravity displacement.
6. No change in the total number and size of demyelinating lesions in the brain as measured by Magnetic Resonance Imagining (MRI)
7. Some degree of reduction of inflammatory activity of demyelinating lesions comparing time 0 as measured by MRI Gadolinium contrast medium uptake and 12 months still pending).

Combined Therapy (Andrographolide and Interferon).

Materials & Methods:

Patients already receiving first-line therapy using interferon beta (IFN-β) were recruited to receive additional combination therapy of oral tablets containing 55 mg of andrographolide, twice a day for 60 months. Of recruited patients, three have to date completed the 60 month treatment period.

Results:

1. Complete safety and tolerability in all patients after 60 months of daily oral intake of 2 mg/kg of Andrographolides, associated to Interferon in combined therapy
2. No relapses during the 60 months, as observed by clinical and neuroimaging follow up.
3. Early symptomatic synergistic effect of the CT on fatigue, strength and equilibrium when andrographolide tablets are administered along with Interferon, as observed between 2-3 months of compound of Formula I administration.
4. Partial, but in some cases significant functional recovery of sensitiveness and neuromotricity, observed between 24 and 30 months, with the Combined therapy (CT)
5. Significant regression of neurological lesions as measured by neuroimaging control between 14 and 24 months with the Combined therapy (CT)
6. All patients report total symptomatic control of pain, fatigue, spasticity and improvement of mood, noticeable already at four months of CT therapy.
7. Patients, who received andrographolide tablets plus Interferon (combined therapy), responded with an earlier and greater effect on improvement of fatigue and motricity
8. Improvement on focal functionality, such as speech impairment (dysarthria) and vision, deglutition (severe neurologic dysphagia) and fine motricity (recovering writing, self eating and hygiene) between months 12-14 with the CT.
9. Improvement in scattered functionality such as fatigue, leg strength, coordination and walking equilibrium with the CT.
10. Antigravity displacement at month 30, beginning perception of initial recovery from this impairment between four and six months with CT.
11. Significant reduction of the size and number of demyelinating lesions in the brain white matter with the CT.
12. Reduction in inflammatory activity of demyelinating lesions as measured by MRI Gadolinium contrast medium uptake with the CT.

Given our disclosure here, the artisan can readily derive variations thereof. For example, one may increase the dose of andrographolide, or substitute one compound of Formula I for another, to achieve a similar effect. We thus intend that the legal coverage of our patent be defined not by our specific examples taught here, but by our appended legal Claims and legally permissible equivalents thereof.

What is claimed is:

1. A method for treating multiple sclerosis in a human patient by providing beta interferon to said a human patient, the improvement comprising administering to said human patient a compound of Formula I:

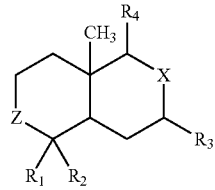

(I)

wherein
- $R_1$ is selected from the group consisting of hydrogen, alkyl or hydroxyl,
- $R_2$ is selected from the group consisting of hydroxyalkyl or alkyl-O-$L_1$, wherein $L_1$ is a carbohydrate moiety,
- $R_3$ is selected from the group consisting of hydrogen or hydroxyl,
- X is selected from the group consisting of $C(=CH_2)$, CH(OH), or a spirooxirane-2 moiety,
- Z is selected from the group consisting of $CH_2$, CH(OH) or $C(=O)$, and
- R4 is selected from the group consisting of an optionally substituted $L_2$-alkyl or $L_2$-alkenyl, wherein $L_2$ is an optionally substituted 3-furanyl or 3-fur-3-enyl moiety, or a pharmaceutically acceptable salt, ester, ether or prodrug thereof.

2. The method of claim 1, wherein the beta interferon ("IFNO") is selected from the group consisting of: purified naturally-occurring IFN, synthetic IFN and recombinant IFN.

3. The method of claim 1, wherein $R_1$ is methyl.

4. The method of claim 1, wherein $R_2$ is selected from the group consisting of: hydroxymethyl and $CH_2$—O—Glc; wherein Glc is a glycoside-forming glucose moiety.

5. The method of claim 1, wherein $R_4$ is selected from the group consisting of: 3-(3-furanyl)-propyl, 3-(3-furanyl)-prop-1-enyl, 3-(3-furanyl)-prop-2-enyl, 3-(3-fur-3-enyl)-propyl or 3-(3-fur-3-enyl)-prop-1-enyl; said 3-furanyl or 3-fur-3-enyl moiety further, optionally substituted.

6. The method of claim 1, wherein $R_4$ is selected from the group consisting of:

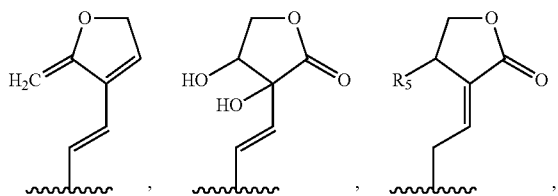

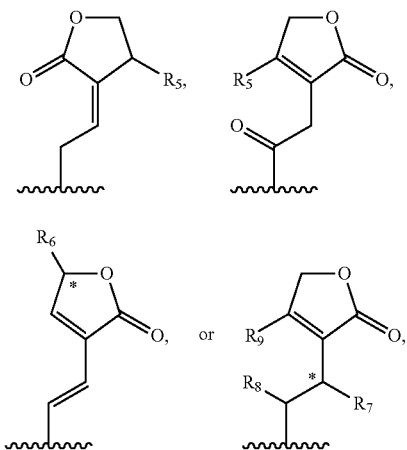

wherein,
- $R_5$ is selected from the group consisting of: hydrogen and hydroxyl;
- $R_6$ and $R_7$ are independently selected from the group consisting of: hydrogen, hydroxyl and alkyloxy; or $R_6$ and $R_7$ are simultaneously replaced by a single direct bond between the carbon atoms denoted by *, thus forming a dimer of two monomer molecules of formula (I), and
- $R_8$ and $R_9$ are independently selected from the group consisting of: hydrogen, hydroxyl and alkyloxy.

7. The method of claim 6, wherein $R_6$, $R_7$, $R_8$ or $R_9$ can be independently methoxy.

8. The method of claim 1, wherein the compound of Formula (I) is selected from the group consisting of andrographolide, neoandrographolide, 14-deoxyandrographolide 14-deoxy-11,12-didehydroandrographolide, andrographiside, andrograpanin, 14-deoxy-11-oxo-andrographolide, 14-deoxy-11-hydroxy-andrographolide, 14-deoxy-12-hydroxy-andrographolide, 3,14-dideoxyandrographolide, 3-oxo-14-deoxyandrographolide, 8,17-epoxy-14-deoxyandrographolide, 14-deoxy-17-beta-hydroxyandrographolide, 12-hydroxyandrographolide, bisandrographolide A, 3-oxo-14-deoxy-11,12-didehydroandrographolide, 7-hydroxy-14-deoxyandrographolide, 15-methoxy-3,19-dihydroxy-8(17) 11,13-ent-labda-trien-16,15-olide, andropanolide, 14-deoxy-12-methoxy-andrographolide, 14-epi-andrographolide, 19-hydroxy-ent-labda-8(17), 13-dien-15,16-olide, 3,11,14,19-tetrahydroxy-ent-labda-8(17), 11-dien-16,15-olide, 3,19-dihydroxy-15-methoxy-ent-labda-8(17), 11,13-trien-16,15-olide, and 3,19-dihydroxy-ent-labda-8(17),12-dien-16,15-olide.

9. The method of claim 1, wherein the beta interferon is provided in an amount of at least about 6 MUI per month and wherein the compound of Formula I is provided in an amount of at least about 50 mg per day.

10. The method of claim 9, wherein the beta interferon is provided in an amount of from about 6 MUI to about 12 MUI per month and wherein the compound of formula I is provided in an amount of from about 50 mg to about 500 mg per day.

11. The method of claim 1, wherein the beta interferon and the compound of Formula I are provided in an amount and for a time sufficient to produce remyelination and to reduce inflammation in said human patient.

12. The method of claim 9, wherein the compound of Formula I is provided in an amount of between about 1 mg and about 5 mg per kilogram of body weight of said human patient.

13. A method to reduce fatigue in a human subject with multiple sclerosis, the method consisting of
administering beta interferon,
administering a compound of Formula I:

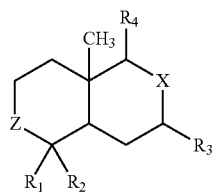

(I)

wherein
$R_1$ is selected from the group consisting of hydrogen, alkyl or hydroxyl,
$R_2$ is selected from the group consisting of hydroxyalkyl or alkyl-O-$L_1$, wherein $L_1$ is a carbohydrate moiety,
$R_3$ is selected from the group consisting of hydrogen or hydroxyl,
X is selected from the group consisting of C(=$CH_2$), CH(OH), or a spirooxirane-2 moiety,
Z is selected from the group consisting of $CH_2$, CH(OH) or C(=O), and
$R_4$ is selected from the group consisting of an optionally substituted $L_2$-alkyl or $L_2$-alkenyl, wherein $L_2$ is an optionally substituted 3-furanyl or 3-fur-3-enyl moiety,
or a pharmaceutically acceptable salt, ester, ether or prodrug thereof, said beta interferon and said compound of Formula I administered in an amount effective to reduce fatigue.

14. The method of claim 13, wherein the effective amount of beta interferon is from about 6 MUI to about 12 MUI of IFN-beta, and wherein the effective amount of compound of Formula I is between about 1 mg and about 5 mg per kilogram of body weight of said human subject.

15. A method comprising:
providing at least one compound of Formula I:

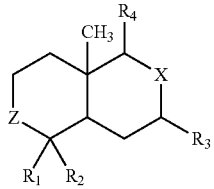

(I)

wherein
$R_1$ is selected from the group consisting of hydrogen, alkyl or hydroxyl,
$R_2$ is selected from the group consisting of hydroxyalkyl or alkyl-O-$L_1$, wherein $L_1$ is a carbohydrate moiety,
$R_3$ is selected from the group consisting of hydrogen or hydroxyl,
X is selected from the group consisting of C(=$CH_2$), CH(OH), or a spirooxirane-2 moiety,
Z is selected from the group consisting of $CH_2$CH(OH) or C(=O), and
R4 is selected from the group consisting of an optionally substituted $L_2$-alkyl or $L_2$-alkenyl, wherein $L_2$ is an optionally substituted 3-furanyl or 3-fur-3-enyl moiety,
or a pharmaceutically acceptable salt, ester, ether or prodrug thereof; and
manufacturing with said compound of Formula I a medicament intended for use in treating a human patient diagnosed as having multiple sclerosis, said medicament intended to be used in combination with beta interferon, said medicament having an amount of said at least one compound of Formula I effective to treat multiple sclerosis.

16. The method of claim 15, wherein said at least one compound of Formula I comprises andrographolide.

17. The method of claim 15, wherein said medicament is in unit dosage form, and wherein said amount effective to treat said multiple sclerosis is not less than about 50 mg per day.

18. The method of claim 17, wherein said amount effective to treat said multiple sclerosis is from about 50 mg to about 500 mg per day.

19. The method of claim 16, wherein said amount effective to treat said multiple sclerosis is from about 50 mg to about 500 mg per day.

* * * * *